US008333749B2

(12) United States Patent
Tsang et al.

(10) Patent No.: US 8,333,749 B2
(45) Date of Patent: Dec. 18, 2012

(54) DISPOSABLE ABSORBENT ARTICLE WITH REGIONS OF VARYING ELASTICITY

(75) Inventors: Patrick Tsang, Kwai Chung (CN); Anne Smid, Wolvega (NL); Andrew Wright, Chesterfield (GB)

(73) Assignee: DSG Technology Holdings Ltd., Tortola (VG)

( * ) Notice: Subject to any disclaimer, the term of this patent is extended or adjusted under 35 U.S.C. 154(b) by 0 days.

(21) Appl. No.: 10/441,639

(22) Filed: May 20, 2003

(65) Prior Publication Data

US 2004/0236299 A1    Nov. 25, 2004

(51) Int. Cl.
*A61F 13/15* (2006.01)
*A61F 13/20* (2006.01)
(52) U.S. Cl. .......... 604/385.27; 604/385.04; 604/385.24
(58) Field of Classification Search ............ 604/385.03–385.05, 385.24–385.29
See application file for complete search history.

(56) References Cited

U.S. PATENT DOCUMENTS

| | | | | |
|---|---|---|---|---|
| 4,210,143 A | * | 7/1980 | De Jonckheere | 604/389 |
| 4,315,508 A | | 2/1982 | Bolick | |
| 4,883,480 A | * | 11/1989 | Huffman et al. | 604/385.27 |
| 4,895,569 A | | 1/1990 | Wilson et al. | |
| 5,204,997 A | | 4/1993 | Sakai et al. | |
| 5,209,743 A | | 5/1993 | Hardison | |
| 5,531,732 A | * | 7/1996 | Wood | 604/391 |
| 5,749,865 A | * | 5/1998 | Yamamoto et al. | 604/385.29 |
| 5,769,835 A | * | 6/1998 | Fell et al. | 604/385.28 |
| 5,899,895 A | * | 5/1999 | Robles et al. | 604/385.29 |
| 5,906,008 A | * | 5/1999 | Heki et al. | 2/400 |
| 6,174,303 B1 | * | 1/2001 | Suprise et al. | 604/385.29 |
| 6,325,787 B1 | * | 12/2001 | Roe et al. | 604/385.27 |
| 6,328,724 B1 | | 12/2001 | Ronnberg et al. | |
| 7,575,573 B1 | * | 8/2009 | Roe et al. | 604/385.29 |
| 2001/0023341 A1 | | 9/2001 | Karami | |
| 2002/0045879 A1 | | 4/2002 | Karami | |
| 2002/0058920 A1 | | 5/2002 | Toyoda et al. | |
| 2003/0009143 A1 | | 1/2003 | Lavon et al. | |
| 2004/0015146 A1 | | 1/2004 | Mori et al. | |
| 2004/0044323 A1 | * | 3/2004 | Roessler et al. | 604/385.24 |

FOREIGN PATENT DOCUMENTS

| | | |
|---|---|---|
| EP | 0-320 989 A | 6/1989 |
| EP | 1 179 331 A | 2/2002 |
| EP | 1 354 576 A | 10/2003 |
| TW | 530634 Y | 5/2003 |
| WO | WO-97/47265 A | 12/1997 |
| WO | WO-02/43636 A | 6/2002 |

OTHER PUBLICATIONS

European Second Examination Report, issued Apr. 1, 2010 (published Apr. 1, 2010) during the prosecution of European Application No. 04 734 064.1-2124.
Taiwan Office Action, issued Jun. 9, 2010 (published Jun. 9, 2010) during the prosecution of ROC (Taiwan) Application No. 093114276.

(Continued)

*Primary Examiner* — Philip R Wiest
(74) *Attorney, Agent, or Firm* — Fulbright & Jaworski L.L.P.

(57) ABSTRACT

A disposable absorbent article with a central body and a pair of elasticized side panels that extend longitudinally along the sides of the central body. Each side panel has a front longitudinal edge and a rear longitudinal edge opposite the front longitudinal edge, and a front or rear fastening element positioned adjacent the front or rear edge. The front edge of the side panel is positioned closer to the front waist portion than the rear edge. The fastening element is constructed for fastening the front and rear waist portions of the central body when the disposable absorbent article is worn by a user. Further, each side panel includes elastic elements that are positioned along the length of the side panel such that the side panel has generally greater elasticity in the vicinity of the rear edge than in the vicinity of the front edge.

29 Claims, 9 Drawing Sheets

OTHER PUBLICATIONS

International Search Report and Written Opinion of PCT/IB2004/002080 dated Nov. 20, 2005, 18 pages.

International Preliminary Report on Patentnabily of PCT/IB2004/0002080 dated Jun. 29, 2005, 12 pages.

* cited by examiner

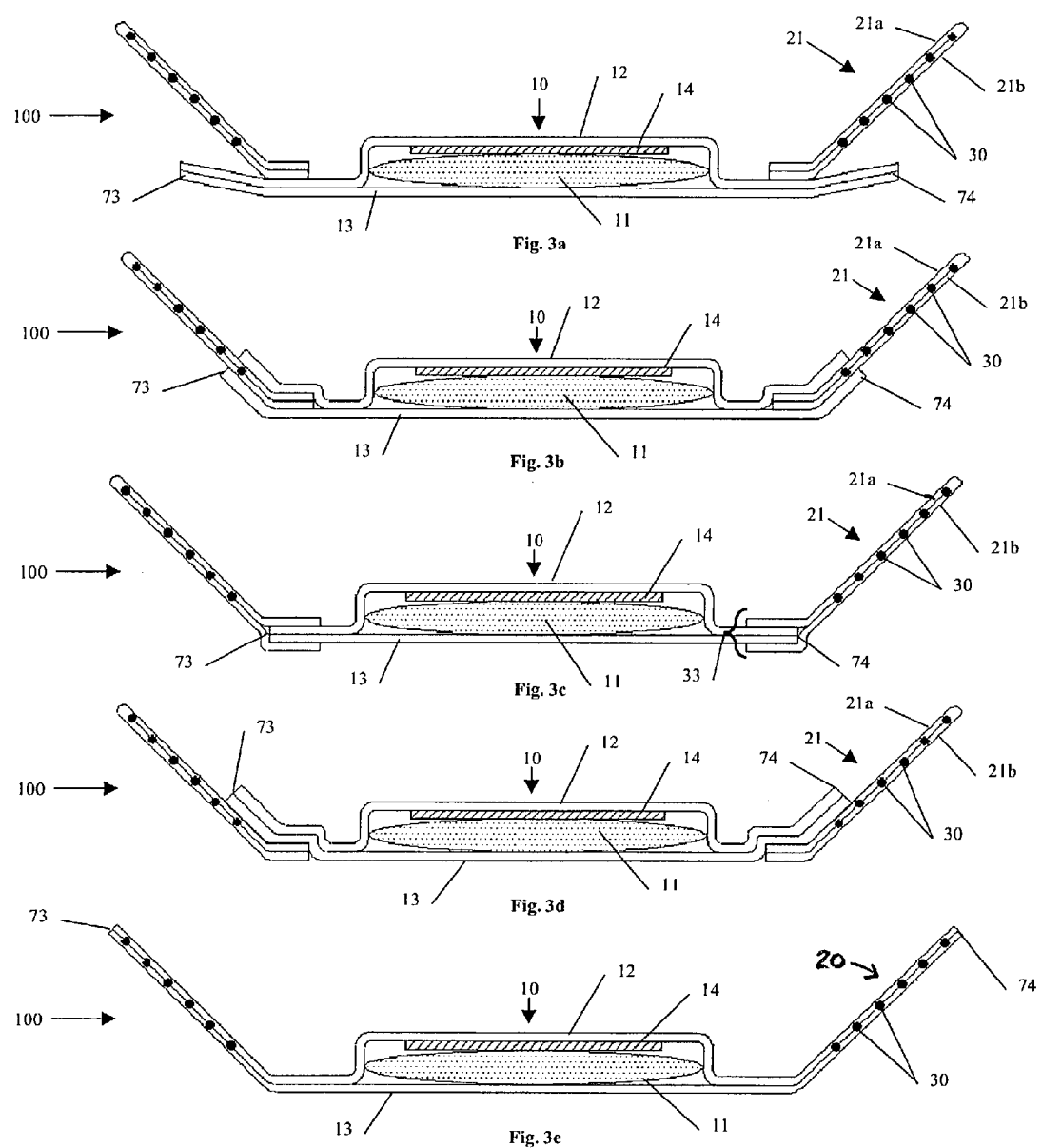

DISPOSABLE ABSORBENT ARTICLE WITH REGIONS OF VARYING ELASTICITY

BACKGROUND OF THE INVENTION

The present invention relates generally to a disposable absorbent article or garment and a method of making the same. More particularly, the invention relates to a disposable absorbent article, such as a baby diaper or disposable pull-on garment, that includes a pair of elasticized side panels for fastening waist portions of the article together.

Disposable absorbent articles are worn to contain and absorb urine and faecal exudates. To this end, an absorbent article incorporates certain components or structural attributes which function to provide a close, comfortable fit around the user's legs and waist. Such a close fit enhances the containment and leakage prevention capabilities of the absorbent article.

Disposable absorbent articles contemplated by the invention are worn about the lower torso or waist of the user so as to receive and contain urine and other bodily wastes. Disposable diapers are particularly intended for use on infants who depend on the caretaker to fit the diaper. Typically, the infant is laid down when the caretaker places the article around the waist region of the infant and then secures two ends together.

Disposable pull-on garments include training pants, pull-on diapers, disposable underwear, and adult incontinence garments. It is generally expected that the user of any one of these garments will be able to put on and take off the garment on his or her own. As for training pants, these garments are intended for use on a young child just before or about the time the child is ready to graduate from diapers to regular underpants. Training pants (and other disposable pull-on pants) have closed sides such that the user or caregiver raises the garment about the user's legs to put it on and slips the garment downward about the user's legs to take it off. Thus, training pants (and other pull-on pants) are designed to be put on and taken off in the same way and manner in which regular underpants are put on and taken off. This feature has particularly been advantageous in toilet training because it provides an early introduction to underpants and, more specifically, trains the child to wear regular underpants.

The principle elements that typically make up the disposal absorbent articles described above are a liquid-permeable inner layer (or topsheet), a liquid-impermeable outer layer (or backsheet), and an absorbent core sandwiched between the inner and outer layers. Elasticized barrier leg cuffs, gathering components, and waistbands are often employed to provide leakage prevention by enhancing the fit of the absorbent article about the thighs and waist of the user. For example, elastic members may be positioned longitudinally along the article, generally outboard of the absorbent core to effect a seal around the legs, buttocks, or both of the user. In addition, several elastic members (e.g., in the form of elongated elastic threads or strands) may be positioned laterally throughout the waist regions (including side waist regions) of the disposable absorbent article to allow the article to stretch when it is put on and then during wear. In this way, the article can stretch to accommodate variations of waist size and leg size of the user, while fitting snugly about the waist and legs and without sagging.

BRIEF SUMMARY OF THE INVENTION

In one aspect of the present invention, a disposable absorbent article has a central body and a pair of elasticized side panels (sometimes referred to herein as stretch panels). The central body includes or provides an absorbent core, and, thus, may be referred to herein as a central absorbent assembly. When disposed in a generally flat, open condition, e.g., before being worn by a user or at a later stage in the manufacturing process, the central body has or is otherwise further characterized by a front longitudinal edge, a rear longitudinal edge opposite the front longitudinal edge, and a longitudinal centerline extending across the front and rear edges. These front and rear edges define, at least partially, front and rear waist portions, respectively, of the disposable absorbent article. The pair of elasticized side panels extends longitudinally adjacent opposite lateral sides of the central body. Each of the side panels also has a front longitudinal edge and a rear longitudinal edge opposite the front longitudinal edge, as well as a front or rear fastening portion formed by the side panel extending longitudinally past a corresponding front or rear edge of the central body. This front or rear fastening portion is constructed or adapted for fastening the front and rear waist portions of the central body when the disposable absorbent article is worn by a user. The invention as described above (i.e., incorporating the described structural elements) is particularly suited for an application to a disposal absorbent diaper.

In another aspect of the invention, side panels incorporated with or into the inventive disposable absorbent article are characterized by an elastic stretch property or elasticity in the longitudinal direction. This elasticity is imparted on the stretch panel by an arrangement of elastic elements along the length of the side panel. The elasticity of the side panel enhances the fit of the disposable absorbent article around the thighs of the user. Further, a disposable absorbent article according to several embodiments of the invention utilizes a side panel as an integral part of the waist fastening structure of the absorbent article, thereby also enhancing the fit of the disposable absorbent article around the waist of the user. In a preferred embodiment of the invention, the side panel provides the sealing function (e.g., of a barrier leg cuff and leg gathers), the fastening function, and the waistband tensioning function for the disposable absorbent article.

In yet another aspect of the invention, the disposable absorbent article has a central body or central absorbent assembly and a pair of elasticized side panels extending longitudinally adjacent opposite lateral sides of the central body. The central body includes an absorbent core, a front longitudinal edge, and a rear longitudinal edge opposite the front longitudinal edge. The front and rear edges define, at least partially, front and rear waist portions of the central body. Each side panel also has a front longitudinal edge and a rear longitudinal edge opposite the front longitudinal edge, as well as a fastening portion for fastening the front and rear waist portions of the central body. Moreover, each side panel includes elastic elements disposed along its length to impart elasticity thereal-ong, and such that the imparted elasticity in the vicinity of the elastic elements varies along the length of the side panel to define distinct regions of elastication. In one embodiment of the invention, these distinct regions include a region of substantially zero elastication.

In a further variation of the invention, the inventive article has a central body and a pair of elasticized side panels. The side panels include elastic elements which are positioned along its length such that the side panel has generally greater elasticity in the vicinity of a rear edge of the side panel (which corresponds with a rear waist portion of the central body) than in the vicinity of a front edge of the side panel (which corresponds with a front waist portion of the central body). Preferably, the elastic elements are positioned such that the elasticity of the side panel generally increases in a direction from the front edge of the side panel to the rear edge. More preferably, the elastic elements are positioned such that the side panel has a distinct region of maximum elasticity located in the vicinity of the rear edge. Most preferably, the elastic elements are positioned such that distinct regions of elastication define, form, or otherwise provide a gradient of varying tension along the length of the side panel when the disposable absorbent article is worn, e.g., such that the tension generally increases in a direction from the front edge to the rear edge.

In yet another aspect of the invention, a method of manufacturing a disposable absorbent article is provided. The method includes the step of providing a central body assembly that includes an absorbent core, a front longitudinal edge, and a rear longitudinal edge that is opposite the front longitudinal edge, whereby the front and rear edges of the central body partially define front and rear waist portions respectively. The inventive method further includes the step of providing a pair of elasticized panels by providing a top layer and a bottom layer, and positioning a plurality of elastic elements between the top and bottom layers. Moreover, the elastic elements are positioned along the length of the side panel to impart elasticity along the length of the side panel in the vicinity of the elastic elements. This includes varying the imparted elasticity along the side panel length to define distinct regions of elastication about the elastic elements. Preferably, the elastic elements are positioned so as to form a gradient of varying tension along the length of the side panel (when the side panel is worn by a user). More preferably, the step of varying the imparted elasticity includes generally increasing the imparted elasticity in the direction from the front edge of the side panel to the rear edge of the side panel. Most preferably, this also includes providing a region of maximum elasticity in the vicinity of the rear edge of the side panel.

Still other embodiments of the inventive disposable article and manufacturing method will become readily apparent to those skilled in the relevant art from the following detailed description of the drawings, wherein the various embodiments of the invention are described by way of illustrating the best mode contemplated for carrying out the invention. The invention is capable of other and different embodiments and its several details are capable of modifications and its several structural or processed details are capable of modifications in various and obvious respects, all without departing from the spirit and the scope of the present invention. Accordingly, the following drawings and detailed description of the drawings are to be regarded as illustrative in nature and not as restrictive.

BRIEF DESCRIPTION OF THE DRAWINGS

FIGS. 3a-3e are cross-sectional views across line 3-3 in FIGS. 1 and 2, illustrating various alternative embodiments of the invention;

DETAILED DESCRIPTION OF THE DRAWINGS

Figure 1:
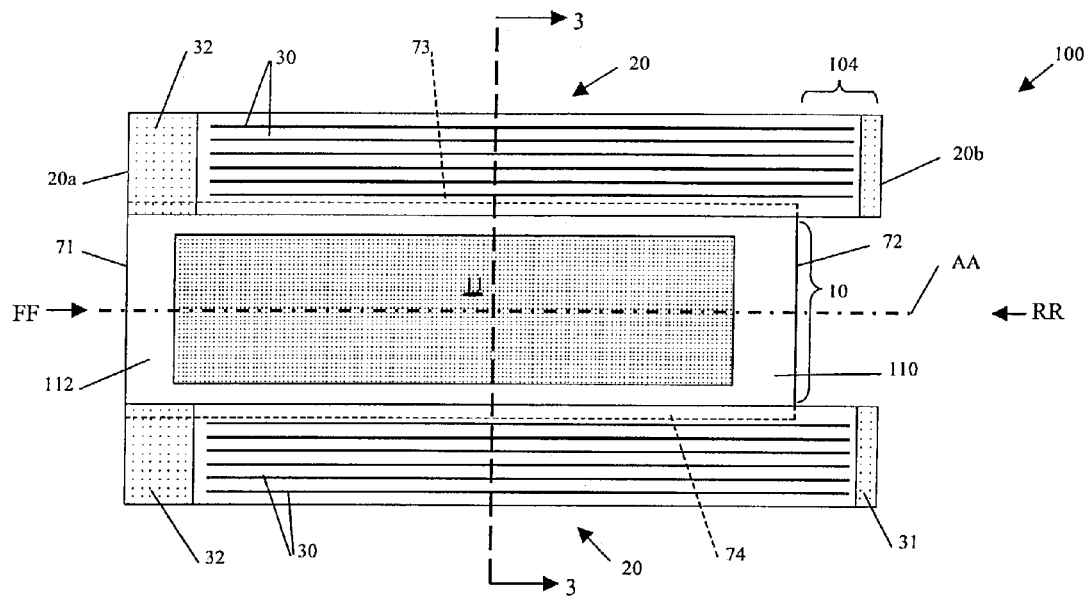
FIG. 1 is a plan view of an inside face of a disposable absorbent article in a generally flat, open condition, according to the present invention.
Figure 2:
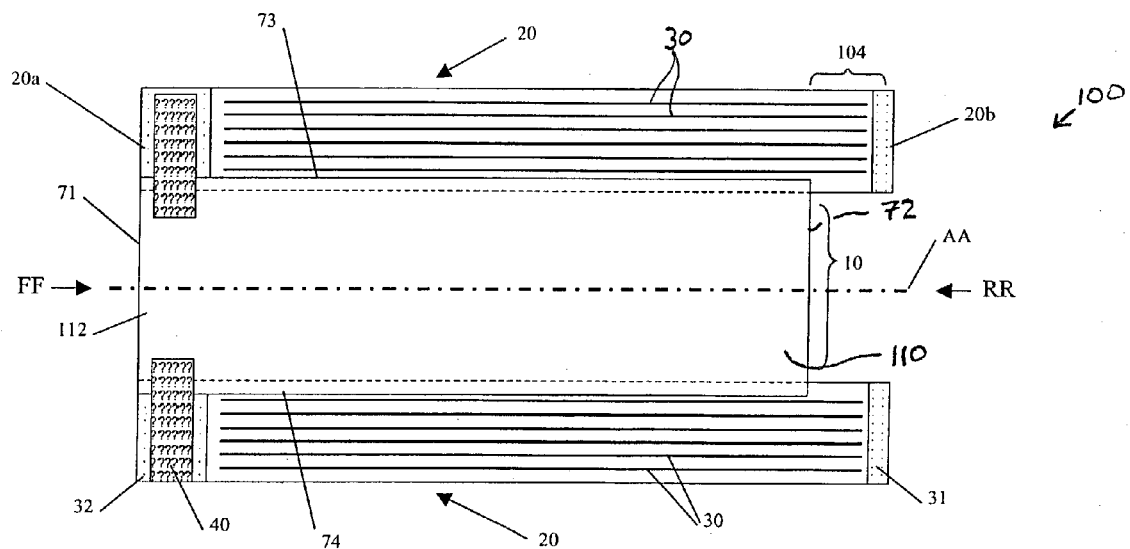
FIG. 2 is a plan view of an outside face of the disposable absorbent article of FIG. 1.

Each of FIGS. 1-8 and 10-14 depicts or illustrates various aspects of a disposable absorbent garment or article 100 according to the present invention and in the form of a disposable diaper. In the various embodiments depicted, like reference numerals are used to indicate like elements. FIGS. 1 and 2 depict the absorbent article 100 in a generally flat, open condition, i.e., the form possibly taken by the article prior to being worn by the user or during a later stage in the manufacturing process. To facilitate the description of the various embodiments, the absorbent article 100 is referred to as having a centrally bisecting longitudinal centerline AA. The article 100 also has a front "FF" and rear "RR" which correspond to the positions taken by the article components in respect to the body of the user when worn.

The inventive disposable absorbent article 100 is preferably of a three-piece/element construction consisting of a central body or absorbent assembly 10 and two longitudinal elastic side panels or stretch panels 20 disposed adjacent opposite lateral sides of the absorbent assembly 10. These longitudinally extending stretch panels 20 may be separately attachable to the absorbent assembly 10 as discussed below.

As will be shown below, the stretch panels 20 provide a sealing function in a manner similar to that associated with conventional barrier leg cuffs and leg gathers. Moreover, the stretch panels 20 according to the invention provide a waist fastening function and a waist or waistband tensioning function for the disposable absorbent article.

Referring also to FIGS. 3a-3e, the absorbent assembly 10 preferably includes an absorbent core 11, a nonwoven liquid-permeable topsheet 12, and a liquid-impermeable backsheet 13. The absorbent assembly 10 may also include an acquisition or surge layer 14, preferably situated between the core 10 and the topsheet 12. The acquisition layer 14 functions to spread out and distribute liquid flow over the core surface. Materials suitable for each of the core 11, topsheet 12, backsheet 13, and acquisition layer 14 and the basic configuration of the absorbent assembly 10 are generally known in the art. Descriptions of some materials and configurations suitable for use with the present invention are found in PCT International Application WO 00/03670 (published Jan. 27, 2000), hereby incorporated by reference and made a part of the present disclosure.

Referring again to FIG. 1, the absorbent assembly 10 has an extended front longitudinal edge 71, a rear longitudinal edge 72, and two side lateral edges 73, 74. The front and rear edges 71, 72 form the longitudinal boundaries and, thus, define, at least partially, front and rear waist portions 112, 110 respectively.

It should first be noted that, upon review of the detailed description and/or the drawings provided herein, it will become apparent to one of ordinary skill in the relevant consumer product art that various aspects of the present invention are also applicable to other disposable absorbent article and garments, and more particularly, to disposable absorbent articles other than disposable diapers. The present invention is not intended to be limited to the structures and manufacturing methods specifically described and illustrated herein.

The stretch panels 20 can be constructed by extending the topsheet 12 and backsheet 13 about a suitable elastomeric element 30. Alternatively, the stretch panels 20 may be constructed from a separate elastomeric material or assembly such as a longitudinal machine direction elastic (MDEL) stretchband 21, that is attached to the absorbent assembly 10. The stretch panel 20 is further characterized by a front longitudinal edge 20a that is positioned on the same end of the article 100 as the front waist portion 112 and a rear longitudinal edge 20b that is positioned on the same end of the article 100 as the rear waist portion 110. In one aspect of the invention, the length and/or position of the stretch panel 20 is such that the front or rear longitudinal edge 20a or 20b of the stretch panel 20 extends beyond the corresponding front or rear longitudinal edge 71 or 72 of the absorbent assembly 10. This extension provides a portion 104 of the stretch panel 20 that advantageously protrudes and extends beyond the corresponding front or rear longitudinal edge 71 or 72 of the absorbent assembly 10.

FIG. 1 illustrates, for example, extended portion 104 extending beyond the corresponding rear edge 72. It should be noted that the term "corresponding" is used to refer to a second component that is positioned similarly (to the first component) at the front or rear of the article 100 and thus identified with the same "front" or "rear" label, e.g., front edge 20a of the stretch panel 20 corresponds with front edge 71 of the absorbent assembly 10. The extension provided by portion 104 helps in fastening the front and rear waist portions 112, 110 of absorbent assembly 10 when the absorbent article 100 is worn by a user. In this respect, the portion 104 is referred to herein as a fastening portion 104, or more particularly, a rear fastening portion 104.

Furthermore, the stretch panel 20 is provided with fastening elements 31, 32 to further facilitate fastening and securing of the front and rear waist portions 112, 110. These fastening elements 31, 32 form a fastening system of the disposable absorbent article 100. During the manufacture of the stretch panel 20, zones or regions having substantially zero elasticity are created, for example, by intermittently applying an adhesive supply. In FIG. 1, these substantially inelastic zones provide a finger-lift area 31 and a landing area 32 upon which to apply a fastening element.

In the embodiment of FIGS. 1 and 2, the fastening system includes another fastening element 40 in the form of a hook fastener, such as that widely used in the art as part of hook and loop fastening systems. When the absorbent article 100 is worn, the fastening portions 104 loop about the thighs of the user and attaches to the front edge 20a of the stretch panel 20 via attachment of hook element 40 (see, e.g., FIGS. 4a-4b and FIG. 5). A nonwoven material used in the construction of the stretch panel 20 acts as the loop element of the fastening system. The hook element 40 is selected to ensure good compatibility with loops formed by the nonwoven material. In alternative embodiments, the article may utilize other known fastening systems, including fastening systems based on pressure sensitive adhesives and silicone release tapes.

Figure 4A:
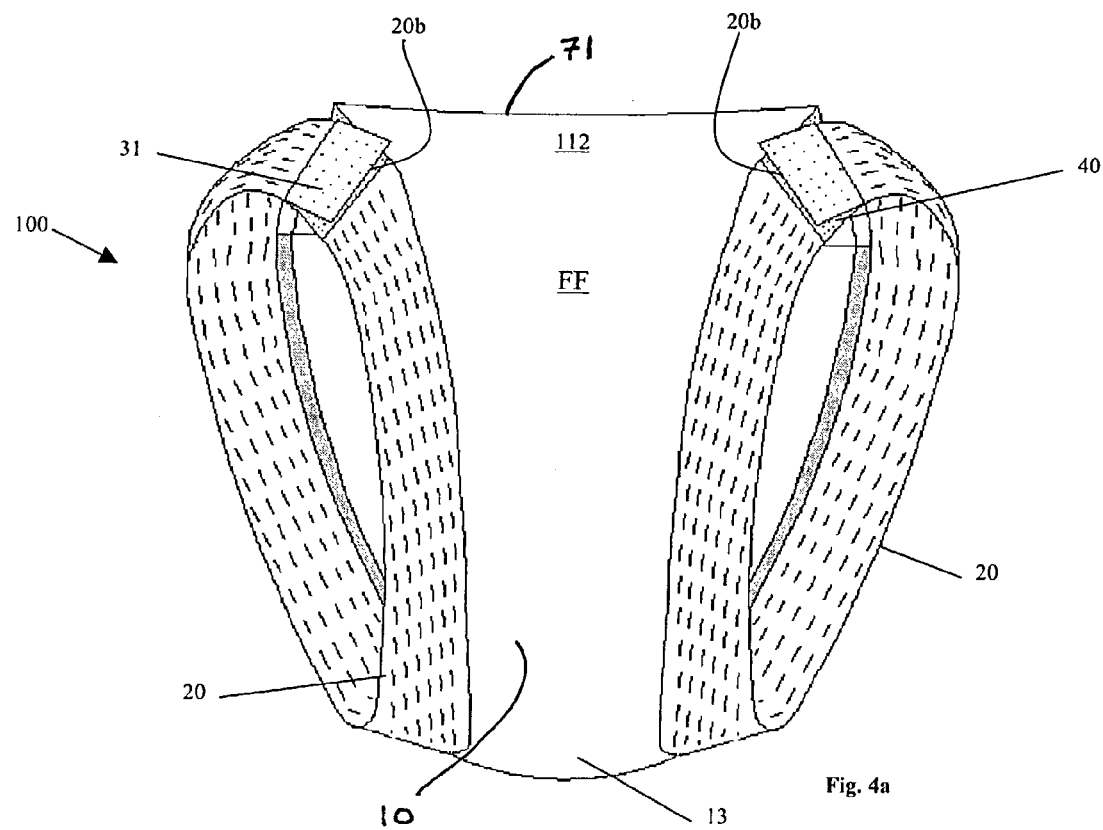
FIGS. 4a and 4b are front and side views, respectively, of the disposable absorbent article of FIG. 1 as it would appear worn by a user.
Figure 4B:
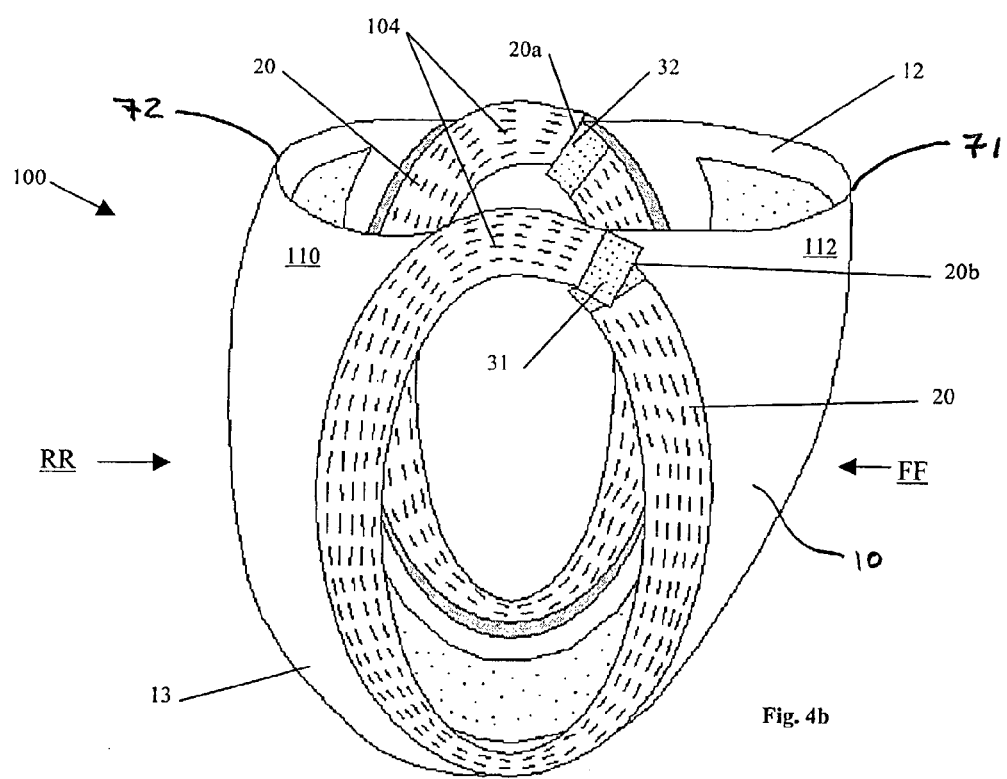
Figure 5:
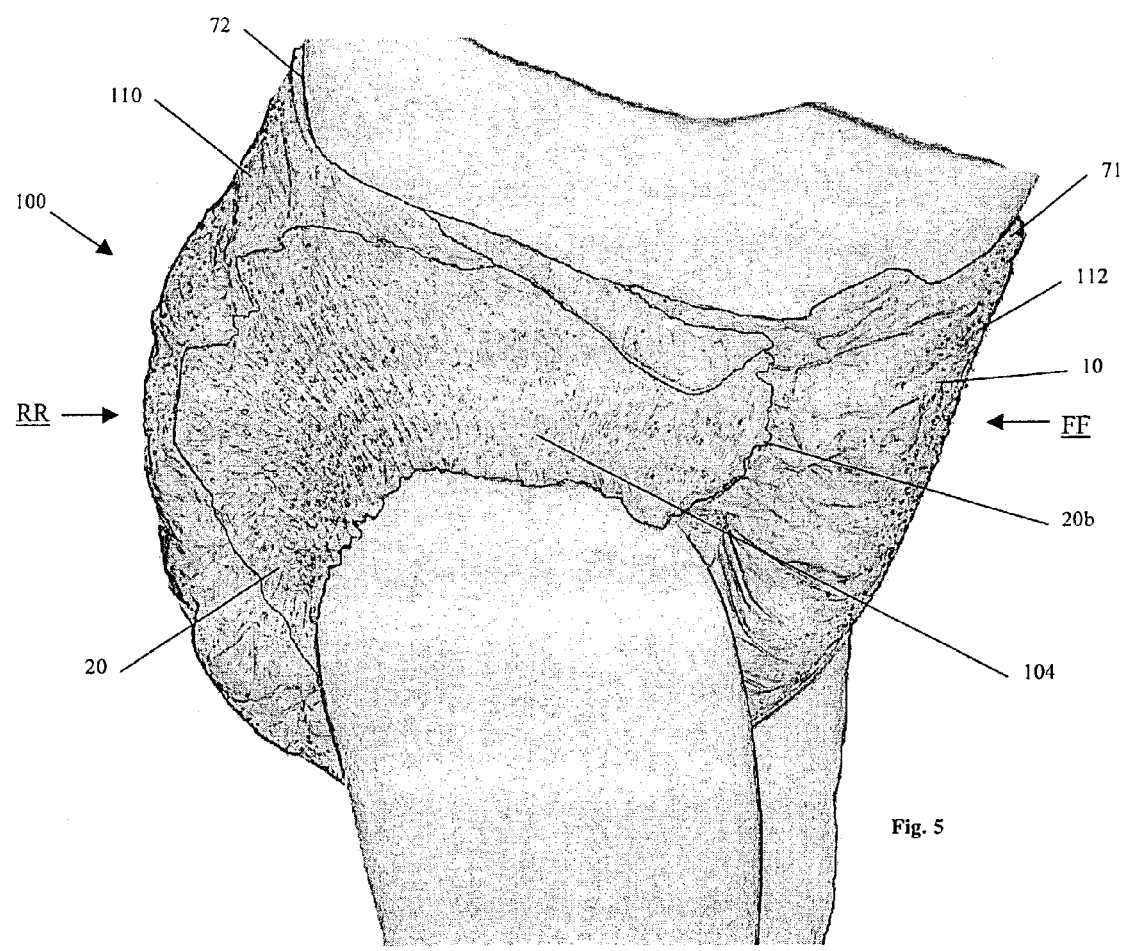
FIG. 5 is an alternative side view of the disposable absorbent article of FIG. 1, as it would appear worn by a user.

FIGS. 4a and 4b depict front and side views of the inventive article 100 as it would appear when worn by a user. The stretch panels 20 are looped around the thighs of the user such that the front and rear edges 20a, 20b mutually engage. In this way, the front and rear waist portions 112, 110 are fastened together, thereby forming an all around waist portion about the user. It should be noted that the front and rear waist portions 112, 110, or more particularly, the front and rear edges 71, 72 of the absorbent assembly 10 do not have to actually contact each other when fastened (see e.g., FIGS. 4 and 5). More importantly, the stretch panels 20 allow for the front and rear waist portions 112, 110 to encircle the waist of the user as shown in FIG. 5. The portions 104 add or extend the front and rear waist portions 112, 110 to form a continuous waist portion encircling the user. This illustrates one way that the fastening portion 104, and thus, the stretch panels 20, facilitates the mutual attachment of the front and rear waist portions 112, 110.

FIGS. 3a-3e are various cross-sectional views of the inventive disposable absorbent article 100. Each of FIGS. 3a-3d illustrates a stretch panel 20 in the form of a separately attachable machine direction elongated stretchband 21. In FIG. 3a, the stretchband 21 is secured in any suitable manner to the nonwoven topsheet 12. In the embodiment of FIG. 3b, the stretchband 21 is attached between the nonwoven topsheet 12 and the backsheet 13. FIG. 3c provides another embodiment of the invention wherein the stretchband 20 includes a selvedge 33 that is attached to the upper surface of the topsheet 12 and the lower surface of the backsheet 13. In the embodiment of FIG. 3d, the stretchband 21 is attached to the backsheet 13. It should also be noted that the stretch panel 20 or stretchband 21 can be attached to the lateral edges of the absorbent assembly 10 using any of the methods for assembling diaper components known to those skilled in the relevant art. Such methods may involve, for example, the use of hot melt adhesive and/or ultrasonic bonding.

FIG. 3e depicts a further variation of the inventive article 100 wherein the lateral edges 73, 74 of the absorbent assembly 10 are extended beyond the absorbent assembly 10 to form the stretch panels 20. Elastomeric elements 30 are disposed between the topsheet 12 and backsheet 13 of the absorbent assembly 10 to impart elasticity to the stretch panels 20. Thus, the stretch panels 20 of FIG. 3e are formed as a unitary part of the absorbent assembly 10 rather than independently thereof, as with the embodiments of FIGS. 3a-3d.

The stretchband 21 is a material assembly that is preferably elasticized in the longitudinal, machine direction, but may also be elasticized in the lateral, cross direction. The material assembly includes a top layer 21a, a base or bottom material layer 21b, and a plurality of elastic elements 30 sandwiched between the top and bottom material layers 21a, 21b. In an alternative embodiment, the stretchband 21 is formed using a single wide layer of nonwoven that is folded over the elastic elements. Typically, the elastomeric elements 30 are elastomeric threads or strands which are pre-tensioned and then glued or otherwise adhered to the top and bottom material layers 21a, 21b. Elastication may also be provided by other elasticizing means known to those skilled in the art, including solid elasticizing films, liquid applied elastomer, elastomeric ribbons, elastic foam, or rubber. The top and bottom material layers 21a, 21b may be provided by a polypropylene, nonwoven material, such as those often used to make the topsheet or leg cuff components of a conventional disposable diaper.

Alternatively, one or both of the top and bottom layers 21a, 21b may be provided by a polyethylene film or laminated nonwoven/film combination such as that used for the backsheet of a conventional disposable diaper. In the stretch panel 20 of FIG. 3e, the topsheet 12 and backsheet 13 provides the top and bottom material layers.

In a preferred embodiment, the stretchband 21 is provided with several longitudinally-extending elastomeric threads or strands 30 which are sandwiched between top and bottom layers 21a, 21b, of a nonwoven fabric. The nonwoven fabric is preferably of a basis weight between about 10 and 100 grams per square meter. Using a hot-melt adhesive, the elastomeric strands 30 are applied to a web of the nonwoven fabric in an elongated pre-tensioned state (e.g., between about 50% and 500% elongation). When the stretchband web is later cut to form discrete stretchbands, the elastomeric strands 30 are also cut and released from sections or regions near the ends of the stretchband 21. Now void of elastomeric material, these end regions become substantially de-elasticized or non-elasticized zones 31, 32. Zones 31, 32 then provide a finger-lift area 31 and a landing area 32 upon which to apply fastening elements.

Figure 6:
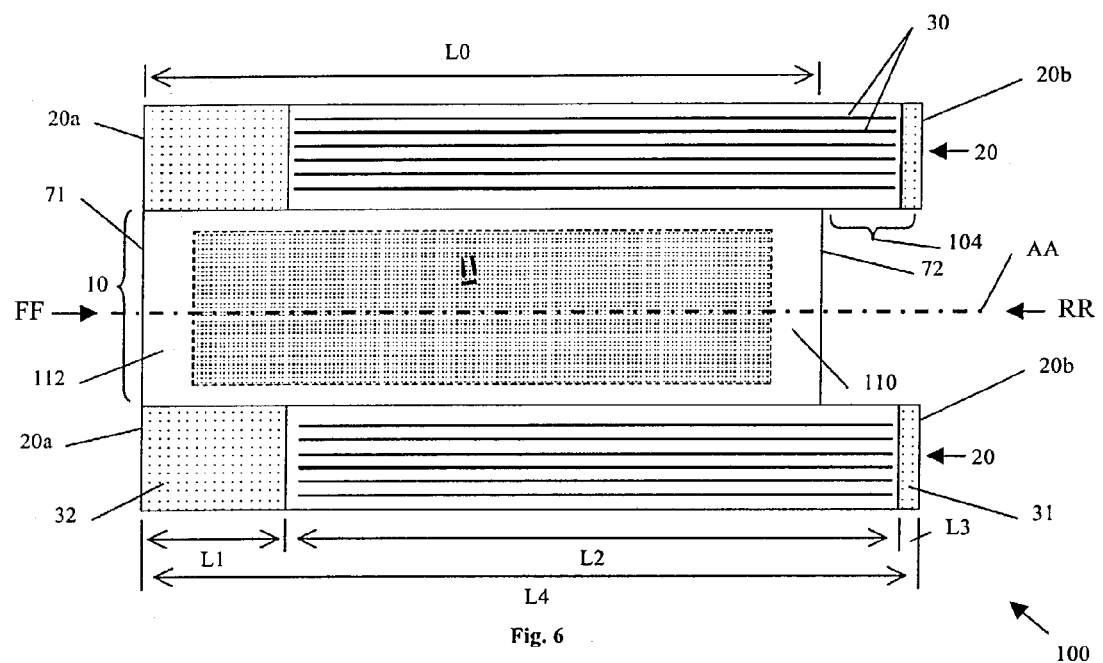
FIG. 6 is a plan view of the disposable absorbent article of FIG. 1, wherein various dimensions are highlighted.

FIG. 6 is a reproduction of FIG. 1 that highlights certain important dimensions of the inventive disposable absorbent article 100. In this embodiment of the invention, the overall extended length L4 of the stretch panel 20 is equal to the lengths L1 and L3 of the substantially non-elastic zones plus the length L2 of the elasticized zone therebetween. Preferably, the length L1 of the front non-elasticized zone is no less than about 5% and no greater than about 60% of the total length L4 of the stretch panel 20. As shown in the Figures, the total length L4 of the stretch panel 20 exceeds the length L0 of the absorbent assembly 10. Further, the stretch panel 20 is positioned to overlap and extend beyond the rear longitudinal edge 72 of the absorbent assembly 10, thereby providing extended fastening portion 104. In this embodiment, the ratio of the total length L4 of the stretch panel 20 to the length L0 of the absorbent assembly 10 is greater than about 1.05 and less than about 1.50.

Figure 7:
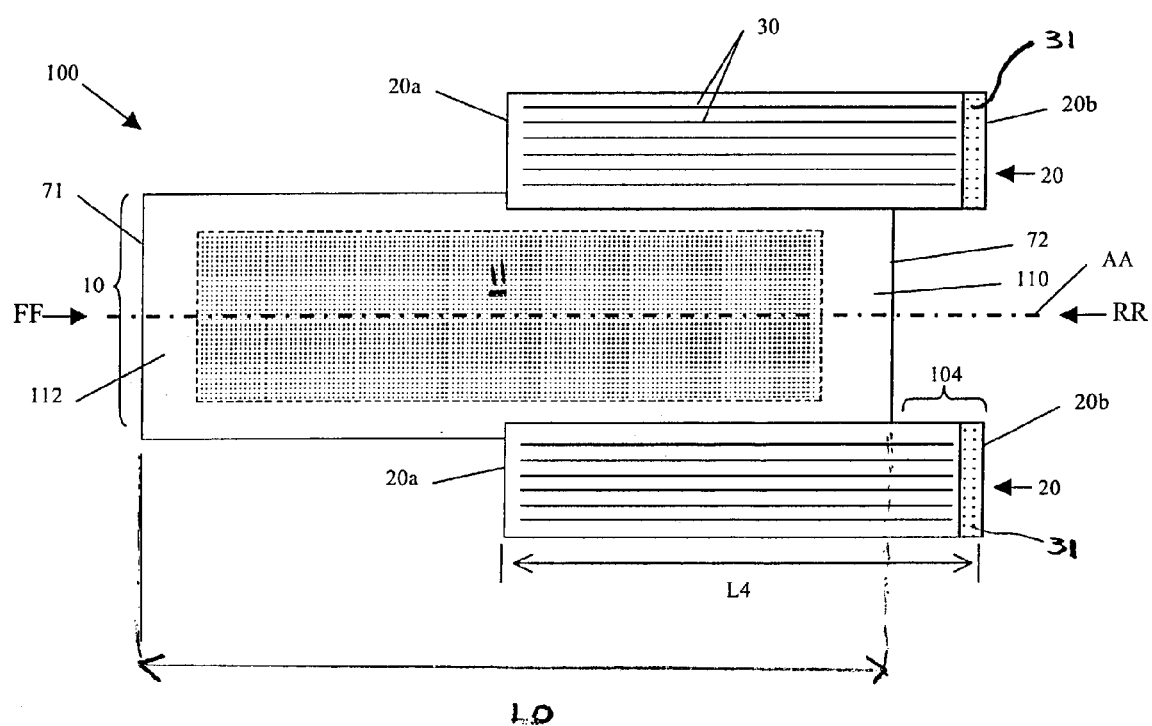
FIG. 7 is a plan view of yet another alternative embodiment of the inventive disposable absorbent article.

In an alternative embodiment of the invention as illustrated by FIG. 7, the total length L4 of the stretch panel 20 is less than the length L0 of the absorbent assembly 10. The stretch panel 20 is again positioned, however, to overlap and extend beyond the rear longitudinal edge 72 of the absorbent assembly 10, thereby providing fastening portion 104. Specifically, the front edge 20a of the stretch panel 20 is positioned intermediate of the front edge 71 and the rear edge 72 of the absorbent assembly 10. In this embodiment, the total length L4 of the stretch panel 20 is preferably between about ½ to 1.0 times the length L0 of the absorbent assembly 10.

The disposable absorbent article according to the present invention provides a close fitting seal around the thighs of the user, thereby significantly improving its leakage prevention capability. Referring now to FIGS. 8a-8d, the close fitting seal of the inventive garment 100 is further enhanced through addition of a fastening element 40 near the front edge 20a of the stretch panel 20. The fastening element 40 is preferably provided by at least one hook fastening device 40 constructed of extruded hooks or mushroom-shaped hooks. More preferably, the hook fastening element 40 is selected so as to be engageable with the microscopic loops formed on the surface of a nonwoven fabric. Thus, the nonwoven material of the stretchband panel provides the loop element of a hook and loop fastening system similar to those generally known in the art.

Figures 8A, 8B, 8C, 8D:
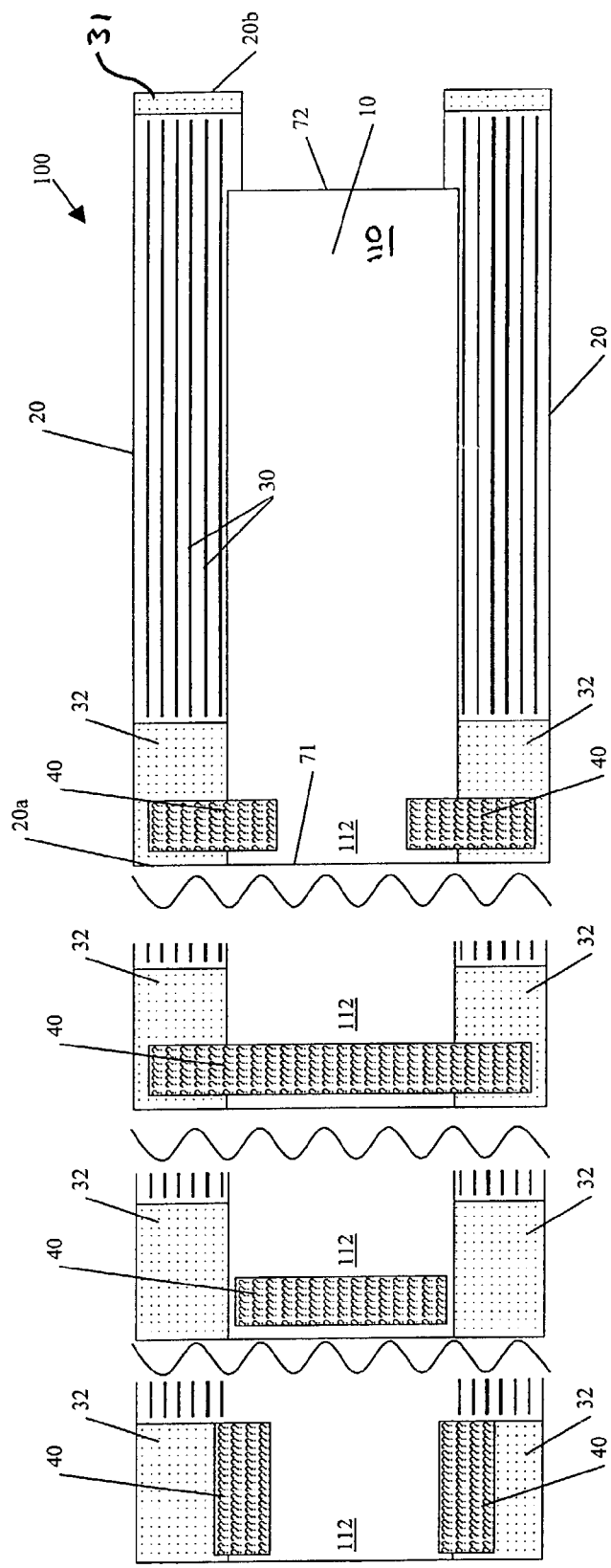
FIG. 8 are plan views of alternative embodiments of the invention incorporating various fastening elements.

FIGS. 8a-8d provide various possible arrangements of the hook fastening element 40 along the front edge 20a of the stretch panel 20. In the first embodiment of FIG. 8a, two laterally extending patches of the hook fastening element 40 is provided near the front edge 20a of each stretch panel 20. In the embodiment of FIG. 5b, the hook fastening element 40 is a single patch that extends across the front waist region 112 of the absorbent assembly 10 and into the non-elasticized zones 32 of the stretch panels 20. In FIG. 8c, the hook fastening element 40 is again a single patch that extends across the front waist region 112 but not over the non-elasticized zones 32. The embodiment of FIG. 8d is similar to that of FIG. 8a, except that the patch of hook fastening element 40 extends longitudinally rather than laterally.

In further embodiments, a loop landing tape may be located near the front waist region 112 of the outside face of the inventive article 100, and a pair of hook fastening elements may be located in the rear non-elasticized zones 32 of each stretch panel 20. The fastening portion 104 is therefore, attached directly to the central body 10 rather than to the front edge 20a of the stretch panel 20. The loop landing tape may be constructed from a knitted, extruded, or non-woven material, as is generally known in the art.

Figure 9:
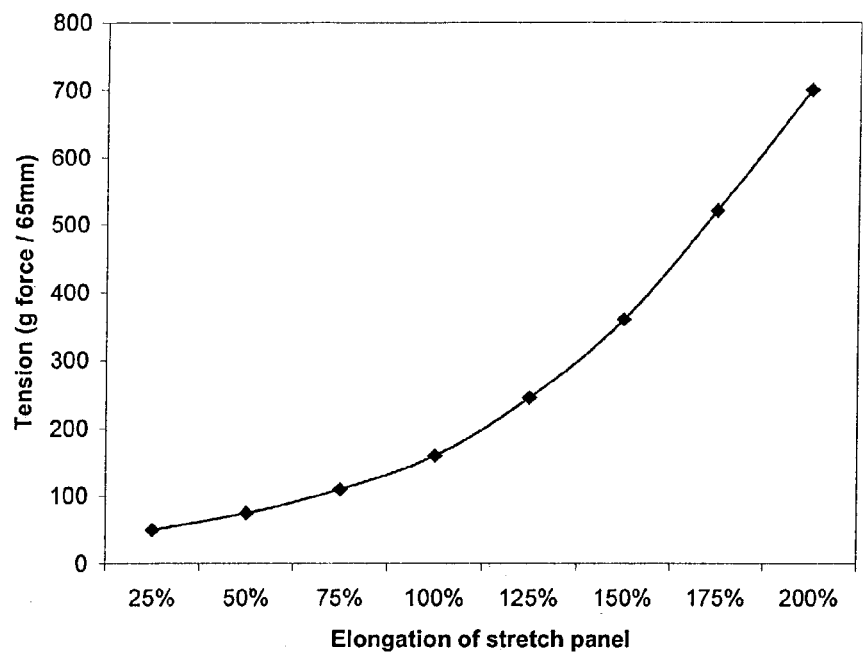
FIG. 9 is a graphical illustration of the overall tension-elongation characteristics of a typical prior art stretch panel.

It is important that the tension forces provided by the stretch panel 20 are neither too low nor too high. If the tension forces geed by the stretch panel 20 are too low, the absorbent article 100 may not fit very closely in certain regions around the legs and the waist and the absorbent article ability to prevent leakage will be compromised. High tension forces may constrict the user's thighs and cause discomfort. In a typical prior art disposable absorbent article, the positioning of elastomeric elements (and the type of elastomeric element placed) does not vary along the length of the stretch panel. The elasticity or elastication of the stretch panel is, therefore, uniform along the stretch panel length. When elongated in a uniform manner, the overall tension provided by the stretch panel is also uniform along its length. The magnitude of this uniform tension depends on the overall elongation of the stretch panel. The chart of FIG. 9 provides the tension generated in the stretch panel for varying degrees of elongation (of the stretch panel). When the absorbent article is worn, however, the elongation of the stretch panel along it length is generally non-uniform, and thus, the tension generated varies. As a result, there may be regions about the length of the stretch panel that are undesirably too loose or too tight.

In accordance with a preferred embodiment of the invention, a disposable absorbent article, or more precisely, a stretch panel, is provided wherein the elasticity and the tension forces generated along the longitudinal length of the stretch panel vary in a predetermined manner. Applicants have discovered that certain predetermined, non-uniform distributions of elastic elements impart a desirable variance in elasticity along the length of the stretch panel. This variance in elasticity provides a desirable tension gradient when the disposable absorbent article is worn by the user. In a further aspect of the present invention, Applicants have also discovered that, by providing certain regions or zones along the length of the stretch panel with a distinct elasticity (imparted by the elastic elements) the fit and sealing capabilities of the absorbent article may be enhanced.

Thus, in one aspect of the invention, the number, type, and/or application of elastomeric strands 30 are varied along the length of the stretch panel 20 such that the elasticity imparted by the elastomeric strands along the stretch panel length also varies. As a result, distinct regions or zones of elasticity are created in the vicinity of the elastomeric strands and along the stretch panel length. The relative elasticity of these distinct regions are generally predetermined to effect a desired tension gradient about the stretch panel when the disposable absorbent article is worn (further discussed below).

In one respect, regions or zones devoid of elastic elements—e.g., zones provided for finger lift area 31 and landing area 32—are also distinct regions of elasticity formed by pre-determined placement of elastic elements. These regions of elasticity differ, however, in the sense that the elastic elements 30 do not impart elasticity to the stretch panel 20 in these regions (in contrast to the distinct regions of imparted elasticity in the vicinity of the elastic elements).

Figure 10:
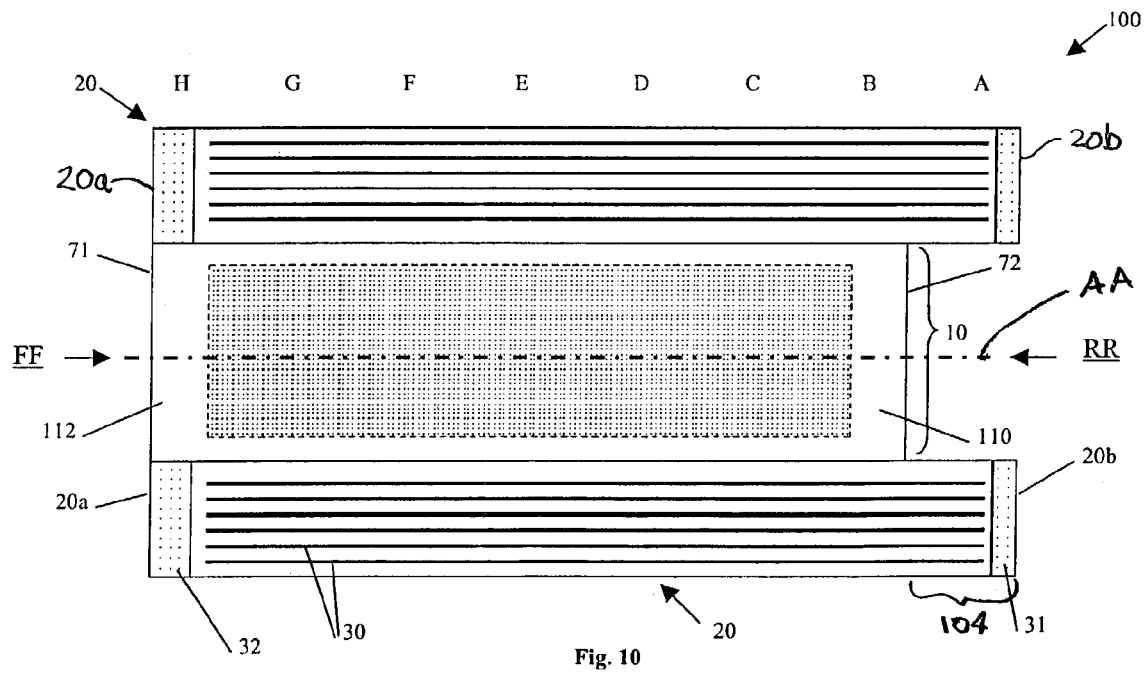
FIG. 10 is a plan view of a first embodiment of the invention, with regions of the stretch panel labeled.
Figure 11:
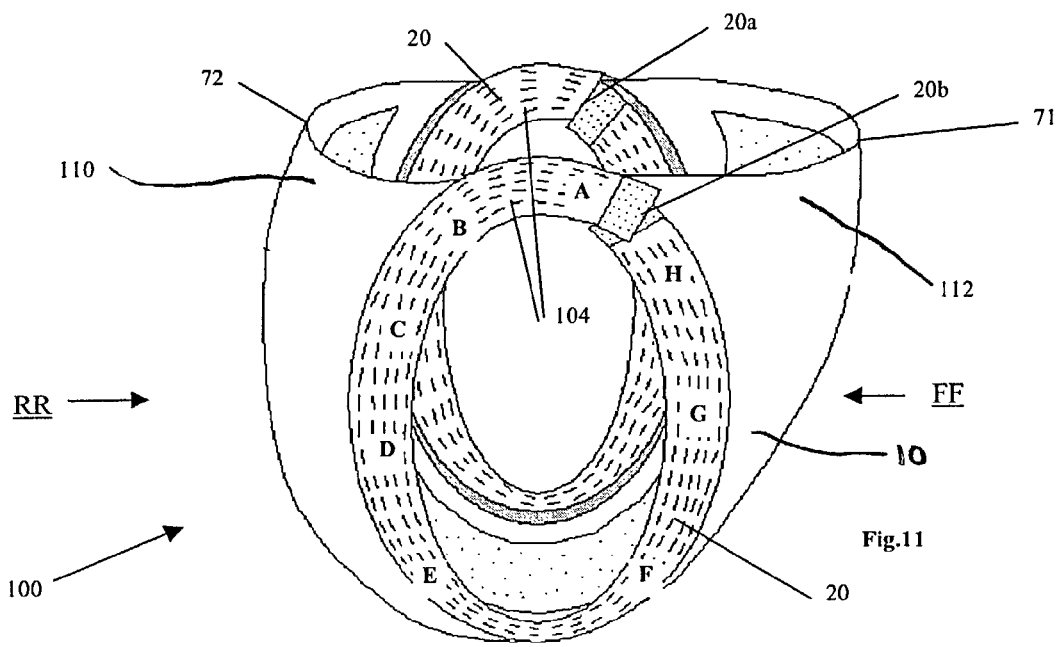
FIG. 11 is a side view of the first embodiment of the inventive disposable absorbent article as it would appear worn by a user and with the stretch panel labeled in correspondence with the plan view of FIG. 10 and the graphical illustration of FIG. 12.

To facilitate the present discussion, FIGS. 10 and 11 provide two views of a disposable absorbent article 100 according to one embodiment of the invention, wherein regions or zones along the longitudinal length of the stretch panel 20 are indicated alphabetically. FIG. 10 provides a view of the disposable absorbent article 100 in a generally flat, open condition. FIG. 11 provides a side view of the disposable absorbent article 100 as it would appear worn by a user, wherein the regions or zones are marked about the stretch panel 20. In both views, the longitudinal length of the stretch panel 20 is marked by reference letters A-H, with A referring to the region or zone nearest the rear edge 20b and reference letter H referring to the region or zone nearest the front edge 20a. The chart of FIG. 12 corresponds with FIG. 11 and indicates the tension provided along the length or loop of the stretch panel 20 in the various regions A-H, when the article is worn by a user.

Figure 12:
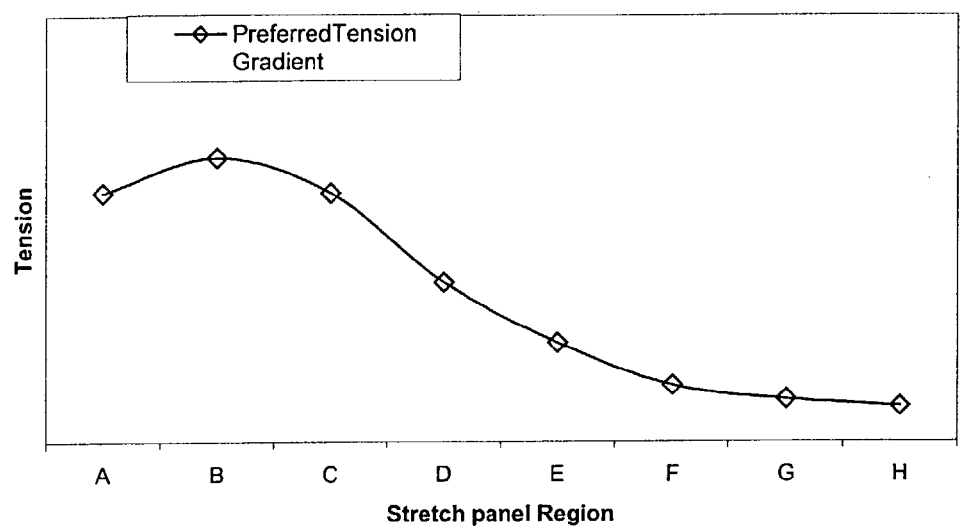
FIG. 12 is a graphical illustration of a tension gradient corresponding with the labeled regions of the stretch panel in FIG. 11.

As illustrated by the chart of FIG. 12, the tension generated by the stretch panel 20 when the article 100 is worn varies advantageously in a pre-determined manner. This variance in tension or tension gradient is obtained by designing the stretch panel 20 so as to have distinct elastic properties along its length. More specifically, distinct regions of elastication are provided by selecting or designing certain characteristics (e.g., pre-tensioning, quantity, concentration, type, etc.) of the elastomeric elements 30 in the various regions, thereby obtaining the desired tension gradient. Preferably, the stretch panel 20 is designed such that a region(s) near the rear edge 20b (i.e., region B) has the greatest elasticity and a region(s) near the front edge 20a has the lowest elasticity (i.e., regions G). Referring to FIG. 12, the combination of the elastic properties of the stretch panel 20 and elongation of the stretch panel 20 when the article 100 is worn, provide a region of maximum tension around region B and a region of minimum tension around region H. It should be noted that the embodiments of FIGS. 10 and 11 utilize one size and type of elastic elements. In alternative embodiments, the type, size, and number of elastic elements may be varied along the stretch panel length.

Preferably, the elasticity and thus the tension associated with the various distinct regions of the stretch panel 20 increases in the direction from the front edge 20a to the rear edge 20b. Referring to FIG. 12, elasticity of the stretch panel 20 is at a maximum in region B, which is in the vicinity of the rear longitudinal edge 20b and adjacent rear edge 72 and rear waist portion 110 of the absorbent assembly 10. Together, regions A, B and C provide regions of the greatest elasticity along the longitudinal length of the stretch panel 20. On the other hand, region H, which is closest to the front edge 20a of the stretch panel 20 and closest to the front waist portion 112 of the absorbent assembly 10, provides a region of minimum elasticity. Accordingly, in a preferred embodiment of the invention, the stretch panel 20 is characterized by tension forces which are significantly greater around the waist and down the back of the thigh of the user, than corresponding regions at the front FF of the disposable absorbent article 100.

Figure 13:
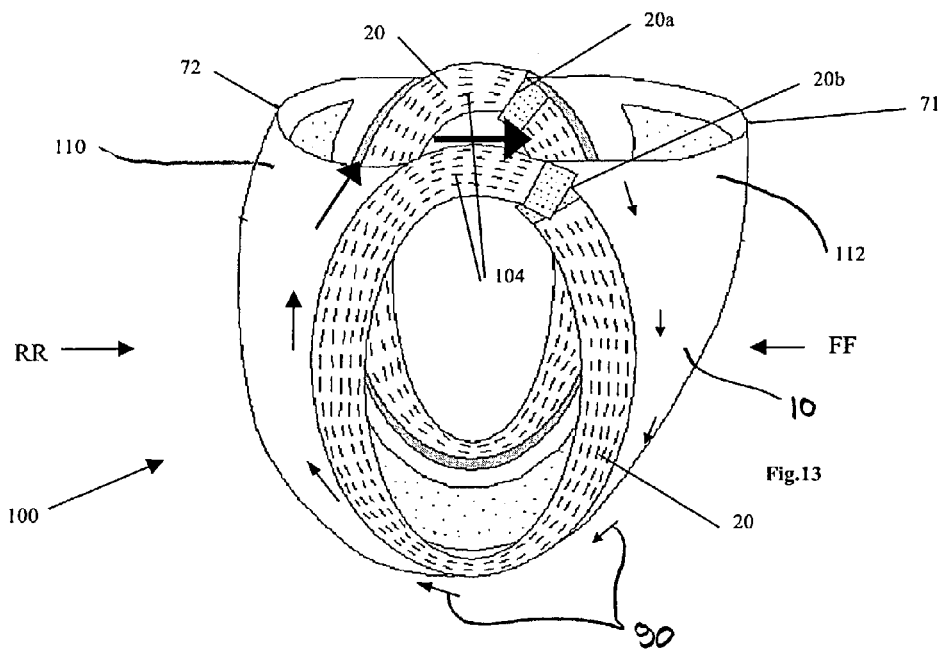
FIG. 13 is a side view of a disposable absorbent article according to the present invention as it would appear worn by a user and with the magnitude of tension forces along the length of the stretch panel represented.

FIG. 13 provides a side view illustration of a disposable absorbent article 100 as worn by a user. In this figure, the size of the arrows 90 indicate the magnitude of the tension forces in that region of the stretch panel 20. As clearly shown therein, the tension forces of the stretch panel 20 increases in the direction from the front edge 20a to the rear edge 20b. One desirable effect of this tension gradient is that the tension generated in the rear portions of the stretch panel 20 (especially in regions A-D) pulls the waist portion 112 toward the user and enhances the seal between the front edge 71 and the user's waist.

Figure 14:
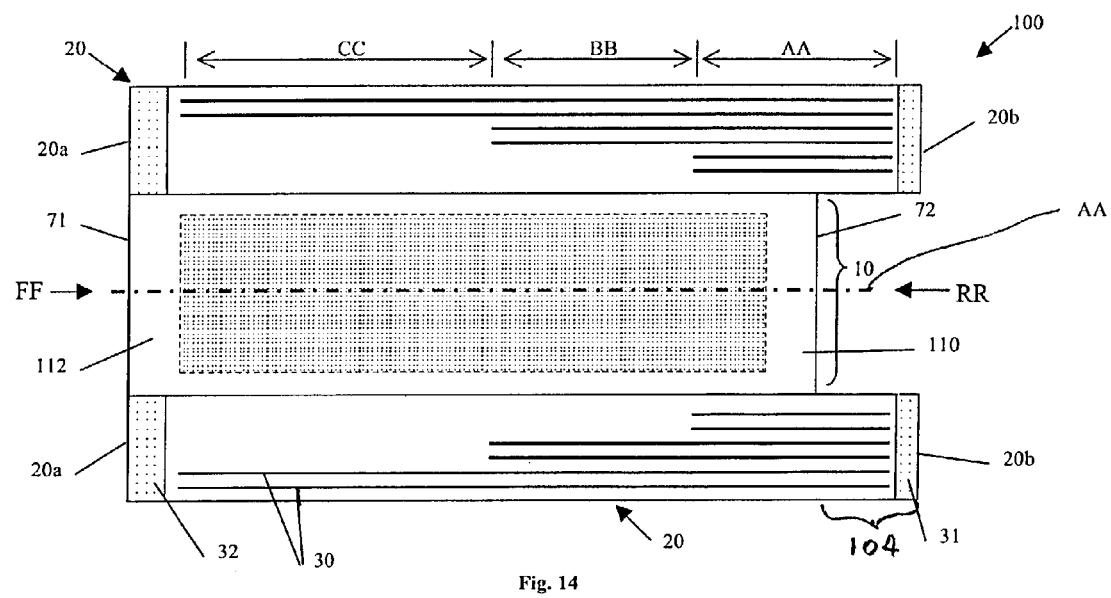
FIG. 14 is a plan view of another alternative embodiment of the invention utilizing varying lengths of elastic strands.

As noted earlier, the elastomeric elements may be varied in types, size, concentration, arrangement, and/or application (to the stretch panel) so as to achieve the desired variance in the elasticity imparted by the elastomeric elements to various regions of the stretch panel. FIG. 14 illustrates one method of achieving such variance.

In the embodiment of FIG. 14, the number of elastomeric strands 30 secured within the stretch panel 20 increases in the direction from the front edge 20a to the rear edge 20b. In region CC (near the front edge 20a), the stretch panel 20 has two elastomeric strands, while in regions BB and AA (near the rear edge 20b), the stretch panel has four and six strands, respectively. Thus, the elasticity imparted on the stretch panel 20 is lowest in the vicinity of the front edge 20a and greatest in the vicinity of the rear edge 20b. Accordingly, the tension generated in the stretch panel 20, when the article 100 is worn, is at a minimum at region CC and at a maximum at region AA.

The stretch panel depicted in FIG. 6 provides a tension gradient similar to that associated with the embodiment of FIG. 13 when the absorbent article 100 is worn by a user. Referring to FIG. 6, the front region or non-elastic zone 32 is void of any elastic elements, and thus, the absorbent article 100 provides a region of minimum elasticity and tension forces near the front edge 20a. Conversely, the stretch panel 20 provides a region of higher elasticity and tension forces near the rear edge 20b. Alternatively, by increasing the area of the non-elasticized zone 32 near the rear edge 20b and decreasing the area of the non-elasticized zone 32 near the front edge, the elasticity and tension forces of the stretch panel 20 will be higher in the front region than in the rear region. The tension gradient generated by such a configuration will be generally the reverse of that represented in FIG. 12.

It should be noted that the preferred embodiment is one wherein the elasticity of the stretch panel generally increases in the direction from the front edge 20a to the rear edge 20a, and wherein the region of maximum of elasticity is provided near the rear edge 20a. As mentioned above, the higher elasticity near the rear edge 20a and along the rear of the disposable garment 100, as shown in FIG. 13, tends to pull the front waist region 112 of the disposable garment 100 towards the waist and body of the user, thereby providing for a closer fit and seal along the front waist region 112. In other embodiments, different arrangements or distributions of elasticity along the length of the stretch panel 20 may be employed to effect a different tension gradient and to address different sealing and comfort concerns.

It is considered that any combination of progressively increasing the lengths of the elastomeric threads and removal of elasticity at the front of the diaper may be used to provide the preferred elastic tension gradient represented in FIG. 12.

The foregoing description of the present invention has been presented for purposes of illustration and description. It is to be noted that the description is not intended to limit the invention to the various apparatus and processes disclosed herein. Various aspects of the invention as described above, may be applicable to other types of disposable absorbent articles and garments, and processes for making the same. For example, the feature of an elasticized side panel having the fastening portion described above, may be incorporated in other disposable absorbent articles such as training pants, etc. Moreover, the feature of an elasticized side panel as having the characteristic elasticity described above may also be incorporated in other disposable absorbent articles and garments. Such variations of the invention will become apparent to one skilled in the relevant consumer products, or other relevant art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A disposable absorbent article disposed in a generally flat, open condition, said disposable absorbent article comprising:

a central body including an absorbent core, a front latitudinal edge, and a rear latitudinal edge opposite said front longitudinal edge, wherein said front and rear latitudinal edges of said central body partially define front and rear waist portions of the disposable absorbent article, respectively, of the disposable absorbent article when worn, and said central body is further characterized by a longitudinal centerline extending across said front and rear latitudinal edges; and a pair of elasticized side panels distinct from said central body and extending longitudinally and adjacent opposite longitudinal sides of said central body a length sufficient to wrap around the legs of a user of the disposable absorbent article when worn, each said side panel having a front latitudinal edge, a rear latitudinal edge opposite said front latitudinal edge, a proximal longitudinal periphery edge, a portion of which is at least co-extensive with said central body, a distal longitudinal periphery edge, and at least one fastening portion for fastening said front and rear waist portions of said central body when the disposable absorbent article is worn by the user, wherein the distal longitudinal periphery edge of the side panels are generally parallel to one another along the length of the side panels;

wherein each elasticized side panel comprises an elastic element, the elastic element providing a direction of stretch to said side panel that is generally parallel to said longitudinal centerline, wherein said elastic element extends longitudinally past a corresponding said front or rear latitudinal edges of said central body, wherein said front latitudinal edge of said side panel is positioned closer to said front waist portion of said central body than to said rear waist portion of said central body, wherein each said side panel includes a front or rear fastening portion formed by said side panel extending longitudinally past a corresponding said front or rear latitudinal edges of said central body, said front or rear fastening portion being constructed for fastening said front and rear waist portions of said central body when the disposable absorbent article is worn by the user, wherein each said fastening portion includes a first fastening element adapted to engage a second fastening element on said central body, wherein the first fastening element is located within the fastening portion and is longitudinally positioned past the latitudinal front or rear edge of said central body such that the fastening element is within the fastening portion in a section thereof which is not coextensive with the central body, and wherein said fastening element is in longitudinal alignment with an elasticized side panel, wherein when the absorbent article is disposed in a relaxed, open and generally flat condition said central body, elasticized side panels and fastening portions all occupy a single plane, wherein the fastening portions are integral to or permanently affixed to the disposable absorbent article, wherein the elastic elements of said side panels are disposed along said length of said side panel to impart elasticity therealong in a longitudinal direction sufficient to cause said side panels to engage the legs of the user when the disposable article is worn, and wherein the amount of said imparted elasticity generally increases from the front to the rear of the legs, said increase in elasticity configured to provide tension at least around said front waist portion when worn.

2. The disposable absorbent article of claim 1, wherein said side panels further include fastening portions of substantially zero elastication positioned longitudinally between said front latitudinal edges of said side panels and said elastic elements.

3. The disposable absorbent article of claim 2, wherein said fastening portions in longitudinal alignment with said elastic elements.

4. The disposable absorbent article of claim 1, wherein said regions of elastication form a gradient of varying tension along the said portion of said length that is wrapped about the legs of the user when said disposable absorbent article is worn.

5. The disposable absorbent article of claim 4, wherein the elastic elements disposed along said length of said side panel to impart elasticity therealong in a longitudinal direction comprise a plurality of elastomeric strands and wherein the regions of elastication are defined by a) the presence of at least one elastomeric strand per region and b) a greater number of elastomeric strands in the side panel at the rear most region than the front most region of the side panel.

6. The disposable absorbent article of claim 5, comprising one or more intermediate side panel regions between the front most and rear most regions, each intermediate region having, from front to rear, a greater number of elastomeric strands than the previous region.

7. The disposable absorbent article of claim 1, wherein said elastic elements are positioned such that the elasticity of said side panel generally increases in the direction from said front edge of said side panel to said rear edge of said side panel.

8. The disposable absorbent article of claim 1, wherein said elastic elements are positioned such that a region of maximum elasticity of said side panel is provided in a vicinity of said rear edge of said side panel.

9. The disposable absorbent article of claim 8, wherein said region of maximum elasticity is adjacent said rear edge of said central body.

10. The disposable absorbent article of claim 1, wherein said elastic element is selected from the group of elastic elements consisting of: solid elasticizing film; liquid-applied elastomer; elastomeric strand; elastomeric ribbon; rubber; elastic foam; and combinations thereof.

11. The disposable absorbent article of claim 1, wherein said elastic elements are elastomeric strands.

12. The disposable absorbent article of claim 11, wherein each said side panel includes a greater number of elastomeric strands in the vicinity of said rear edge of said side panel than in the vicinity of said front edge of said side panel.

13. The disposable absorbent article of claim 11, wherein each said side panel includes thicker elastomeric strands in the vicinity of said rear edge of said side panel than in the vicinity of said front edge of said side panel.

14. The disposable absorbent article of claim 11, wherein each said side panel includes a greater concentration of elastomeric strands in the vicinity of said rear edge of said side panel than in the vicinity of said front edge of said side panel.

15. The disposable absorbent article of claim 11, wherein each said side panel include regions provided with elastomeric strands and fastening portion without elastic strands.

16. The disposable absorbent article of claim 11 wherein said elastomeric strands are disposed between two layers of nonwoven material, said elastomeric strands are attached to the two layers of nonwoven material along the length of the elastomeric strands.

17. The disposable absorbent article of claim 1, wherein said fastening portion is a rear fastening portion that extends past said corresponding rear edge of said central body.

18. The disposable absorbent article of claim 17, wherein said elastic elements are positioned such that a region of maximum elasticity of said side panel is provided in a vicinity of said rear fastening portion.

19. The disposable absorbent article of claim 1, wherein said central body includes a topsheet and a backsheet, said side panels being formed by extensions of said topsheet and said backsheet.

20. The disposable absorbent article of claim 1 wherein said fastening portion has an outward facing periphery edge, a latitudinal periphery edge and an inward facing periphery edge, said inward facing and outward facing periphery edges are in parallel alignment with said longitudinal centerline, and wherein the outward facing, longitudinal periphery edge of said fastening portion is colinear with the longitudinal periphery edge of said side panel and the inward facing longitudinal periphery edge of said fastening portion is extended perpendicularly from the latitudinal front or rear edge of said central body.

21. A disposable absorbent article disposed in a generally flat, open condition, said disposable absorbent article comprising:

a central body including an absorbent core, a front latitudinal edge, and a rear latitudinal edge opposite said front longitudinal edge, wherein said front and rear latitudinal edges of said central body partially define front and rear waist portions of the disposable absorbent article, respectively, of the disposable absorbent article when worn, and said central body is further characterized by a longitudinal centerline extending across said front and rear latitudinal edges; and a pair of elasticized side panels distinct from said central body and extending longitudinally and adjacent opposite longitudinal sides of said central body a length sufficient to wrap around the legs of a user of the disposable absorbent article when worn, each said side panel having a front latitudinal edge, a rear latitudinal edge opposite said front latitudinal edge, a proximal longitudinal periphery edge, a portion of which is at least co-extensive with said central body, a distal longitudinal periphery edge, and at least one fastening portion for fastening said front and rear waist portions of said central body when the disposable absorbent article is worn by the user, wherein the distal longitudinal periphery edge of the side panels are generally parallel to one another along the length of the side panels;

wherein each elasticized side panel comprises an elastic element, the elastic element providing a direction of stretch to said side panel that is generally parallel to said longitudinal centerline, wherein said elastic element extends longitudinally past a corresponding said front or rear latitudinal edges of said central body, wherein each said side panel includes a front or rear fastening portion, said front or rear fastening portion being constructed for fastening said front and rear waist portions of said central body when the disposable absorbent article is worn by the user, wherein each said fastening portion includes a first fastening element adapted to engage a second fastening element on said central body, wherein the first fastening element is located within the fastening portion and is longitudinally positioned past the latitudinal front or rear edge of said central body such that the fastening element is within the fastening portion in a section thereof which is not coextensive with the central body, and wherein said fastening element is in longitudinal alignment with an elasticized side panel, wherein the elastic elements of said side panels are disposed along said lengths of said side panels to impart elasticity therealong in a longitudinal direction sufficient to cause said side panels to engage the legs of the user when the disposable article is worn, wherein the amount of said imparted elasticity generally increases from the front to the rear of the legs, said imparted elasticity being configured to provide tension at least around said front waist portion when worn and wherein said fastening portions are configured to cause each of the side panels to engage a complete circumference of a leg of the user with an elastic leg gather when the disposable article is worn and the first and second fastening elements are engaged.

22. An absorbent article comprising:

a central body with opposite longitudinal edges, a front lateral edge, and a back lateral edge, said front and back lateral edges forming respective front and back waist portions of said absorbent article; and a pair of elasticized side panels attached to the opposite longitudinal edges of the central body, said elasticized side panels extending longitudinally, each said side panel having a front latitudinal edge, a rear latitudinal edge opposite said front latitudinal edge, a proximal longitudinal periphery edge, a portion of which is at least co-extensive with said central body, a distal longitudinal periphery edge, and at least one fastening portion configured to fasten the front waist portion and the back waist portion of the absorbent article around a user when the absorbent article is worn by the user, wherein the distal longitudinal periphery edge of the side panels are generally parallel to one another along the length of the side panels;

wherein each elasticized side panel comprises an elasticity that generally increases from the front to the rear of the legs, said increase in elasticity configured to provide tension at least around said front waist portion when worn;

wherein said elastic side panels extend longitudinally past a corresponding said front or rear latitudinal edges of said central body, wherein said front latitudinal edge of said side panel is positioned closer to said front waist portion of said central body than to said rear waist portion of said central body, wherein said at least one fastening portion of said elasticized side panels includes a first fastening element adapted to engage a second fastening element disposed on said absorbent article, wherein the first fastening element is longitudinally positioned past the corresponding latitudinal front or rear edge of said central body, and wherein said fastening element is in longitudinal alignment with an elasticized side panel.

23. The absorbent article of claim 22, wherein each said elasticized panel comprises at least one of: solid elasticizing film; liquid-applied elastomer; elastomeric strand; elastomeric ribbon; rubber; elastic foam; or combinations thereof.

24. The absorbent article of claim 23, wherein each said elasticized panels comprises elastomeric strands.

25. The absorbent article of claim 23, wherein each said side panel comprise a greater number of elastomeric strands in the vicinity of said rear edge of said side panel than in the vicinity of said front edge of said side panel.

26. The absorbent article of claim 23, wherein each said side panel comprises thicker elastomeric strands in the vicinity of said rear edge of said side panel than in the vicinity of said front edge of said side panel.

27. The absorbent article of claim 23, wherein each said side panel comprises a greater concentration of elastomeric strands in the vicinity of said rear edge of said side panel than in the vicinity of said front edge of said side panel.

28. The absorbent article of claim 23, wherein said elastomeric strands are disposed between a first layer of nonwoven material and a second layer of nonwoven material, said elastomeric strands are attached to the two layers of nonwoven material along the length of the elastomeric strands.

29. The absorbent article of claim 28, wherein said first layer of nonwoven material comprises a topsheet of said central body and said second layer of nonwoven material comprises a backsheet of said central body.

* * * * *